(12) United States Patent  
Bartsch

(10) Patent No.: US 9,125,246 B2  
(45) Date of Patent: Sep. 1, 2015

(54) HEATABLE GLAZING INSPECTION

(75) Inventor: Ingo Bartsch, Dorsten (DE)

(73) Assignee: PILKINGTON AUTOMOTIVE DEUTSCHLAND GMBH, Witten (DE)

( * ) Notice: Subject to any disclaimer, the term of this patent is extended or adjusted under 35 U.S.C. 154(b) by 636 days.

(21) Appl. No.: 13/391,344

(22) PCT Filed: Aug. 20, 2010

(86) PCT No.: PCT/EP2010/062183  
§ 371 (c)(1),  
(2), (4) Date: Feb. 20, 2012

(87) PCT Pub. No.: WO2011/026740  
PCT Pub. Date: Mar. 10, 2011

(65) Prior Publication Data  
US 2012/0147178 A1    Jun. 14, 2012

(30) Foreign Application Priority Data

Aug. 21, 2009    (GB) .................................. 0914651.5

(51) Int. Cl.  
*H04N 7/18* (2006.01)  
*H05B 3/84* (2006.01)  
(Continued)

(52) U.S. Cl.  
CPC ................ *H05B 3/84* (2013.01); *G01N 21/958* (2013.01); *H05B 2203/017* (2013.01)

(58) Field of Classification Search  
CPC ..... G01N 21/88; G01N 25/72; G01N 21/958; G01R 31/00; H04N 7/18; H05B 3/84; H05B 2203/017; G02B 27/18; G02B 13/16; G02B 17/08; G02B 13/10; G02B 3/02; G02B 17/045

USPC .............. 348/125, E7.085, 92, 130; 382/141; 250/341.1; 356/239, 392  
See application file for complete search history.

(56) References Cited

U.S. PATENT DOCUMENTS 4,395,677 A    7/1983    Petersdorf  
5,059,860 A  * 10/1991    Sato et al. ..................... 313/488  
(Continued)

FOREIGN PATENT DOCUMENTS

CN    1759308 A    4/2006  
CN    1761870 A    4/2006  
(Continued)

OTHER PUBLICATIONS

Search Report dated Nov. 5, 2009, issued by the United Kingdom Patent Office in corresponding United Kingdom Patent Application No. GB0914651.5 (4 pages).

(Continued)

*Primary Examiner* — Dave Czekaj  
*Assistant Examiner* — Dramos I Kalapodas  
(74) *Attorney, Agent, or Firm* — Buchanan Ingersoll & Rooney PC

(57) ABSTRACT

A method of inspecting a heatable glazing is disclosed. A heatable glazing comprises a heater array having at least one heater wire. The method comprises the steps of (i) illuminating the heatable glazing with a light source to produce a shadowgraph image of the heatable glazing; (ii) passing a sufficiently high electrical current through the heater array such that the heater wire is observable in the shadowgraph image of the heatable glazing, such a shadowgraph image of the heatable glazing being referred to as an active shadowgraph image of the heatable glazing; and (iii) capturing the active shadowgraph image of the heatable glazing with an imaging sensor. Apparatus for carrying out the method is also disclosed.

14 Claims, 7 Drawing Sheets

(51) Int. Cl.
*G01N 21/958* (2006.01)
*G01N 21/88* (2006.01)

(56) References Cited

U.S. PATENT DOCUMENTS

| | | | |
|---|---|---|---|
| 5,694,479 A * | 12/1997 | Guering et al. | 382/141 |
| 6,205,200 B1 * | 3/2001 | Boyer et al. | 378/101 |
| 6,208,412 B1 * | 3/2001 | Ladewski | 356/239.1 |
| 6,431,711 B1 * | 8/2002 | Pinhanez | 353/69 |
| 6,891,980 B2 * | 5/2005 | Gerhard et al. | 382/321 |
| 7,186,952 B2 * | 3/2007 | Degand et al. | 219/203 |
| 7,596,242 B2 * | 9/2009 | Breed et al. | 382/103 |
| 7,676,062 B2 * | 3/2010 | Breed et al. | 382/100 |
| 7,738,678 B2 * | 6/2010 | Breed et al. | 382/100 |
| 2003/0151739 A1 * | 8/2003 | Capaldo et al. | 356/239.1 |
| 2003/0185976 A1 * | 10/2003 | Villarreal et al. | 427/248.1 |
| 2004/0124358 A1 * | 7/2004 | Okamura et al. | 250/341.1 |
| 2007/0008522 A1 * | 1/2007 | Hill et al. | 356/239.1 |
| 2007/0036464 A1 * | 2/2007 | Hill et al. | 382/286 |
| 2007/0282506 A1 * | 12/2007 | Breed et al. | 701/45 |
| 2014/0064445 A1 * | 3/2014 | Adler | 378/43 |

FOREIGN PATENT DOCUMENTS

| | | |
|---|---|---|
| EP | 0 529 222 A2 | 3/1993 |
| EP | 1 672 960 A1 | 6/2006 |
| GB | 972453 | 10/1964 |
| JP | 6-249905 A | 9/1994 |
| SU | 280956 A1 | 3/1970 |
| WO | WO 2004/083835 A1 | 9/2004 |
| WO | WO 2004/088294 A1 | 10/2004 |

OTHER PUBLICATIONS

"Inspection of Heatable Automotive Wind Screens", graphikon, URL: http://www.graphikon.de/archiv/files/B-GG-L-E-10_06-WiredWindScreen_1.pdf, (available at least as early as Aug. 5, 2009) (1 page).

G.S. Settles, "Schlieren and Shadowgraph Techniques—Visualizing Phenomena in Transparent Media", Springer-Verlag, (2001), pp. 154-159.

International Search Report (PCT/ISA/210) issued on Oct. 14, 2010, by European Patent Office as the International Searching Authority for International Application No. PCT/EP2010/062183.

Office Action (Notification of the First Office Action) issued on Dec. 2, 2013, by the State Intellectual Property Office of the People's Republic of China in corresponding Chinese Patent Application No. 201080036998.0, and an English Translation of the Office Action. (20 pages).

Decision on Grant issued on Nov. 7, 2014, by the Russian Federal Service on Intellectual Property in corresponding Russian Patent Application No. 2012110596/28(015912), and an English Translation of the Office Action. (12 pages).

* cited by examiner

HEATABLE GLAZING INSPECTION

The present invention relates to the optical inspection of vehicle glazings, in particular to the optical inspection of a heatable laminated glazing comprising an array of heater wires laminated between a pair of glass sheets.

In the automotive field, it is well known that windscreens have a laminated construction for safety reasons. A standard feature of a vehicle is the inclusion of a fan assembly designed to blow air onto the inner surface of the vehicle windscreen to demist the inner surface, thereby removing condensation from the inner surface thereof and improving the driver's visibility through the glazing. In particularly cold weather, when ice may form on the inner or outer surfaces of the vehicle windscreen, it is well known that the fan may be used to remove the ice from the windscreen by blowing warm air onto the windscreen, thereby de-icing the windscreen.

In addition to the fan assembly, some vehicles may also have a heatable windscreen, wherein laminated between the plies of the windscreen is a heater array that is connectable to the car battery. The heater array comprises a plurality of spaced electrical conductors, each in the form of fine wires, often known as heater wires. When the electrical connection between the heater array and the car battery is made, an electrical current passes through the heater array causing the heater wires to heat up. This provides localised heating of the windscreen in the vicinity of the heater array that is sufficient to remove ice from the windscreen. Such electrically heatable windows may be installed in cars, boats, aircraft and buildings. A construction of a laminated transparent panel incorporating heater wires is described in GB 972,453. Often in the art such heatable windows are referred to as heated windows.

An important consideration in the construction of such heatable laminated glazings is that the heater array is able to uniformly remove ice and/or condensation from the glazing surfaces. When such a heatable glazing is used as a vehicle windscreen, the vehicle manufacturer usually specifies the requirements of the heater array, such as the electrically resistance of the wires, the material characteristics of the wires, the configuration of the wires (whether straight or not), the thickness of each wire, the length of each wire, the number of active heater wires and their separation. Usually the heater wires are uniformly spaced from the top of the windscreen to bottom i.e. they should be parallel, wherein the top of the windscreen refers to that edge nearest the roof of the vehicle in the installed position. Due to the procedure used to manufacture such a heatable glazing, it is possible that pairs of heater wires in the array may contact each other, thereby electrically shorting out and as a consequence not providing a sufficiently uniform heating. Additional problems may be that the heater array has missing heater wires, heater wires that cross or heater wires that are inoperative for other reasons.

Prior to installing such a heatable glazing, for example a heatable windscreen in a car, it is desirable to inspect the heater array to ensure that the characteristics are acceptable so that the heater array is able to adequately function.

In a related technical field, it is known to inspect a heater grid printed on a surface of a vehicle glazing by passing an electrical current through the heater grid and using a thermal imaging camera to produce a temperature distribution profile. Such a system does not have particularly high spatial resolution and is not suitable for use with embedded heater wires as is the case with laminated heated windscreens. Additionally such systems are not able to resolve the individual heater wires since only global temperature profiles are obtained. An example of such a system is described in US2004/0124358A1.

In JP6249905A, a method and apparatus for inspecting blur-protected glass is disclosed. The apparatus comprises a detection part that brings a roller into contact with the glass being measured. The roller scans the glass a slice at a time. A photoelectric sensor detects the number of electricity feeding filaments. Such a method of inspection is slow because the glazing is scanned a line at a time, thereby taking a long time to make measurements.

Commercially available systems are available for inspecting heatable automotive windscreens. Such systems are able to inspect the function of each individual heating wire. A system known as G/GLAS Wired windscreen inspection is supplied by Graphikon GmbH of Mandelstr. 16, 10409 Berlin, Germany (www.graphikon.de). The inspection system consists of a motorized scanning unit which is driven along the glass. The exact distance of the scanning unit to the glass surface is controlled automatically by a non-contact sensor. The system detects inactive and missing wires. Such a system suffers from the problem that in order to detect defective heater wires, the windscreen is scanned a line at a time. To map a portion of the entire heated area requires the portion to be scanned in a raster fashion which is a time consuming process.

There is therefore a need for a method and apparatus for inspecting a heatable glazing, in particular a laminated heatable vehicle windscreen that comprises a heater array laminated between a pair of glass plies, which at least partially overcomes the problems of known inspection systems.

Accordingly the present invention provides from a first aspect a method of inspecting a heatable glazing, the heatable glazing comprising a heater array comprising a heater wire, the method comprising the steps (i) illuminating the heatable glazing with a light source to produce a shadowgraph image of the heatable glazing;

(ii) passing a sufficiently high electrical current through the heater array such that the heater wire is observable in the shadowgraph image of the heatable glazing, such a shadowgraph image of the heatable glazing being referred to as an active shadowgraph image of the heatable glazing; and (iii) capturing the active shadowgraph image with an imaging sensor.

It has been found that when a sufficiently high electrical current is passed through the heating wires of the heater array that is laminated between the plies of a heatable vehicle windscreen, the heater wires are observable in the shadowgraph image. Without being bound by any particular theory, it is thought that as the heater wire gets hot due to the passage of electrical current therethrough, the refractive index of the surrounding medium changes allowing the heater wire to be observable in the shadowgraph image.

When the heater wire is observable in the shadowgraph image, such a shadowgraph image is referred to as an active shadowgraph image. The electrical current that is passed through the heater should be sufficient such that the heater wire is observable in the shadowgraph image. When insufficient electrical current passes through the heater wire, the heater wire is not observable in the shadowgraph image. In the above method, step (ii) may precede step (i).

A method in accordance with the first aspect of the present invention allows the heater array in a heatable glazing to be rapidly inspected.

Preferably the active shadowgraph image is projected onto a screen, and the imaging sensor captures the active shadowgraph image that is projected onto the screen.

In alternative embodiments of the first aspect of the present invention, the active shadowgraph image is not projected onto a screen, but is instead projected onto a plane in space, and the imaging sensor focuses onto the plane in space to capture the active shadowgraph image.

In other embodiments of the first aspect of the present invention, the method comprises the step of illuminating the glazing when insufficient electrical current is passing through the heater array such that the heater wire is not observable in the shadowgraph image, thereby producing a reference shadowgraph image of the heatable glazing, capturing the reference shadowgraph image, and comparing the active shadowgraph image of the heatable glazing with the reference shadowgraph image of the heatable glazing.

Preferably no electrical current passes through the heater array when the reference shadowgraph image is produced.

Preferably the reference shadowgraph image is captured before the active shadowgraph image. This ensures that the heatable glazing is at ambient conditions when the reference shadowgraph image is captured.

By comparing the active shadowgraph image with the reference shadow image, a difference shadowgraph image may be produced. This has the advantage that by carrying out subsequent analysis on the difference shadowgraph image, the effects of dirt on the surface of the glazing may be reduced, as may other optical effects associated with defects in the body of the glazing, such as bubbles and ream that may contribute to the active shadowgraph image making subsequent analysis difficult. It has been found that these spurious effects can be almost entirely removed by measuring the reference shadow graph image with little or no electrical current passing through the heater array and removing the effects of the reference shadowgraph image from the active shadowgraph image. The reference shadowgraph image of the heatable glazing may be subtracted from the active shadowgraph image of the heatable glazing. Alternatively, the active shadowgraph image of the heatable glazing may be divided by the reference shadowgraph image of the heatable glazing.

Usually the heater array comprises a plurality of heater wires. Preferably the method is used to determine the average spacing of the heater wires.

Preferably the method is used to determine the existence of a non-functioning heater wire.

Preferably the imaging sensor is part of a camera, preferably a digital camera.

The present invention also provides from a second aspect an apparatus for inspecting a heater wire laminated within a heatable glazing, the apparatus comprising a light source for illuminating the heatable glazing to produce a shadowgraph image of the glazing, an imaging sensor to acquire the shadowgraph image and a power supply for applying sufficient electrical current to the heater wire such that the heater wire is observable in the shadowgraph image of the glazing.

From a third aspect, the present invention provides use of a shadowgraph image for inspecting a heatable glazing comprising a heater array having at least one heater wire.

Embodiments of the present invention will now be described by way of example only with reference to the following figures (not to scale) in which, FIG. 1 shows a schematic representation of a heatable vehicle windscreen;

FIG. 3b is a plan view of the apparatus shown in FIG. 3a;

Figure 1:
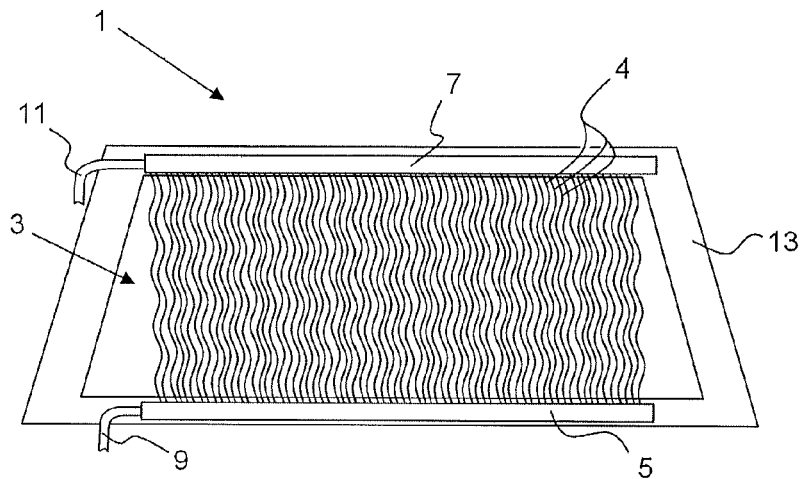

FIG. 1 shows a schematic representation of a heatable vehicle windscreen 1. The heatable vehicle windscreen 1 consists of two panes of glass with a PVB interlayer extending between the panes. There is a heater array 3 comprising a plurality of heater wires 4 laminated in between the glass panes (for clarity, only three of the heater wires are indicated by reference numeral 4). The heater wires are spaced from one another in a substantially uniform manner, being arranged such that adjacent wires do not contact one another. The heater wires are not linear, having an approximate sinusoidal configuration, as is common in the art. Linear heater wires may be used. Typically each heater wire is less than 0.1 mm thick and they are configured such that the heater array has sufficient heating when connected to the car battery. The dimensions of the heatable vehicle windscreen 1 are such that the major face is about 2 m wide by 1 m tall. Typically a heatable vehicle windscreen is between 4 mm and 6 mm thick, having a typical construction comprising two 2.1 mm thick sheets of float glass joined by a PVB interlayer having a thickness of 0.76 mm.

The heater array is arranged to be connectable to a power supply so that electrical current may pass through each heater wire, thereby heating the wire. The lower ends of each heater wire 4 are electrically connected to lower busbar 5. The upper ends of each heater wire 4 are electrically connected to upper busbar 7. Each busbar 5, 7 has a respective lead 9, 11 connected thereto. The heater array is connectable to a power supply via the busbars 5, 7 by connecting each lead 9, 11 to the terminals of the power supply. Instead of the busbars 5, 7 other suitable electrical connection means may be used, for example, additional wires, cables, leads, tags, plugs, spades and their corresponding sockets.

Located around the periphery of the windscreen is a band of screen print 13, usually black in colour (for clarity the band of screen print is shown in white in FIG. 1). The band of screen print 13 is used to obscure the busbars that supply power to the heater wires. Usually the band of screen print is referred to as an obscuration band. Additionally the obscuration band serves to hide the receiving flange of the vehicle bodywork when the windscreen is glazed in position in the appropriate aperture in the vehicle.

The heater array 3 is configured such that when a sufficiently high electrical current is passed through the heater wires, the wires become hot and are able to demist or de-ice the windscreen.

The characteristics of the heater array that may be of concern to a vehicle manufacturer includes the separation of individual heater wires, the average separation of all the heater wires in the array, the number of non-functioning heater wires (for example due to a missing heater wire or a broken heater wire), the number of heater wires in between non-functioning heater wires and the number of heater wires in contact. Depending upon the particular vehicle manufacturer, the relevant criteria required to assess functionality of the heatable vehicle windscreen may vary.

In an alternative configuration, the heatable vehicle windscreen may comprise two adjacent heater arrays, each heater array being independently heatable, each having a pair of busbars associated therewith. In such a configuration, there is a small gap between the adjacent heater arrays.

Figure 2:
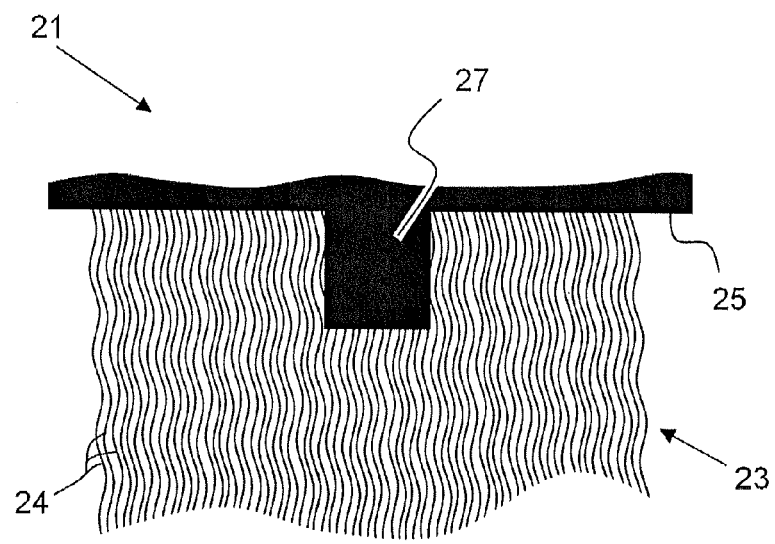
FIG. 2 shows an upper portion of a heatable vehicle windscreen.

FIG. 2 shows an upper portion of another heatable vehicle windscreen 21. As for the heatable vehicle windscreen 1, there is a heater array 23 comprising a plurality of heater wires 24 laminated in between a pair of glass plies in a manner known to one skilled in the art. For clarity, only three heater wires are indicated by reference numeral 24. There is a black obscuration around the periphery of the heatable vehicle windscreen (only a portion of the obscuration band 25 is shown).

Extending from the obscuration band 25 toward the central region of the windscreen is another screen printed region 27 that covers a portion of the inner surface of the windscreen, thereby making it not possible to view the heater wires beneath the screen print in that region.

Figure 3A:
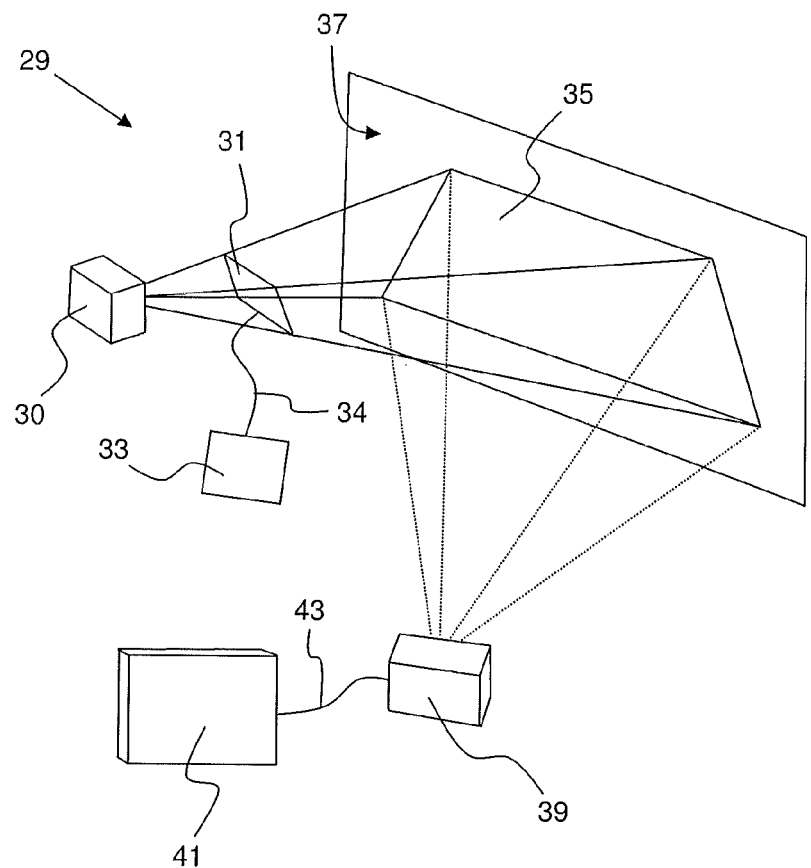
FIG. 3a shows a schematic representation of an apparatus used to inspect the heater array in a heatable vehicle glazing.

FIG. 3a shows a schematic representation of an apparatus used to inspect the heater array of a heatable vehicle glazing. The apparatus 29 comprises an electric arc lamp 30 for illuminating the heatable vehicle windscreen 31. The heatable vehicle windscreen is of the type as described with reference to FIG. 1. The heater array of the heatable vehicle windscreen is in electrical communication with a power supply 33 via cable 34. The power supply may be a conventional 12V car battery. Light from lamp 30 is transmitted through the glazing 31 and casts a shadowgraph 35 onto the screen 37. A digital camera 39 is arranged to collect light reflected off the screen, thereby acquiring an image of the shadowgraph. The digital camera 39 is in electrical communication with a computer 41 via a suitable cable 43. Shadowgraph images acquired by the digital camera are stored and subsequently analysed by the computer. The apparatus 29 is located in a dark room environment to reduce effects of ambient light and to make the shadowgraph easily viewable on the screen 37. The power supply 33 must be able to supply a sufficiently high electrical current such that the heater wires are viewable in the shadowgraph image 35 that is projected onto screen 37 when illuminated by lamp 30.

Figure 4:
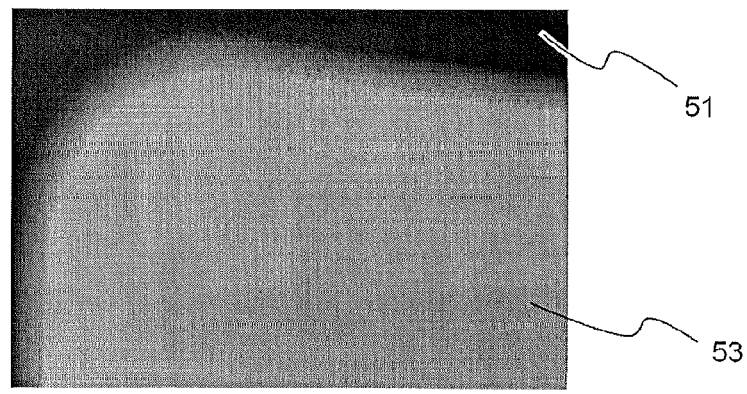
FIG. 4 is a photograph of a shadowgraph image of a heatable vehicle windscreen wherein the heater wires are not observable.
Figure 5:
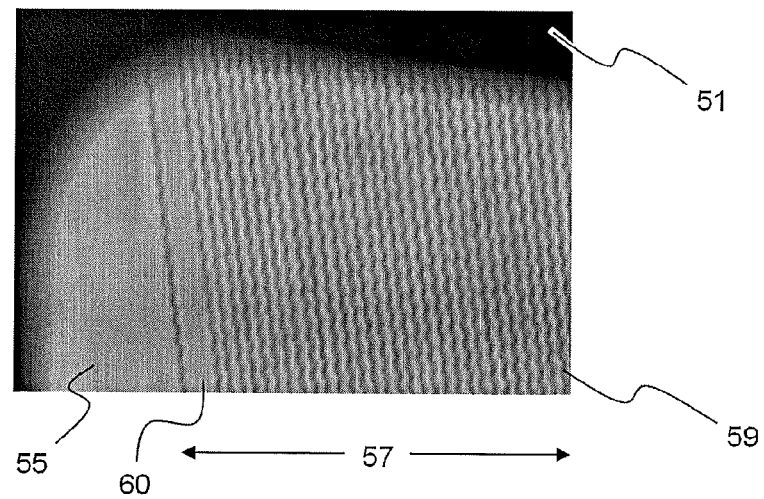
FIG. 5 is a photograph of a shadowgraph image of a heatable vehicle windscreen wherein the heater wires are observable.

When no electrical current is passed through the heater array wires, it is difficult to identify the shadow of the individual wires in the shadowgraph image, as shown in FIG. 4. When a sufficiently high current is passed through the wires, for example by connecting the heater array to a conventional 12V car battery, and the glazing is illuminated, the individual heater wires are observable in the shadowgraph image, as shown in FIG. 5. The electrical current supplied to the heater array may be adjusted to make the heater wires easier to view in the shadowgraph image.

Figure 3B:
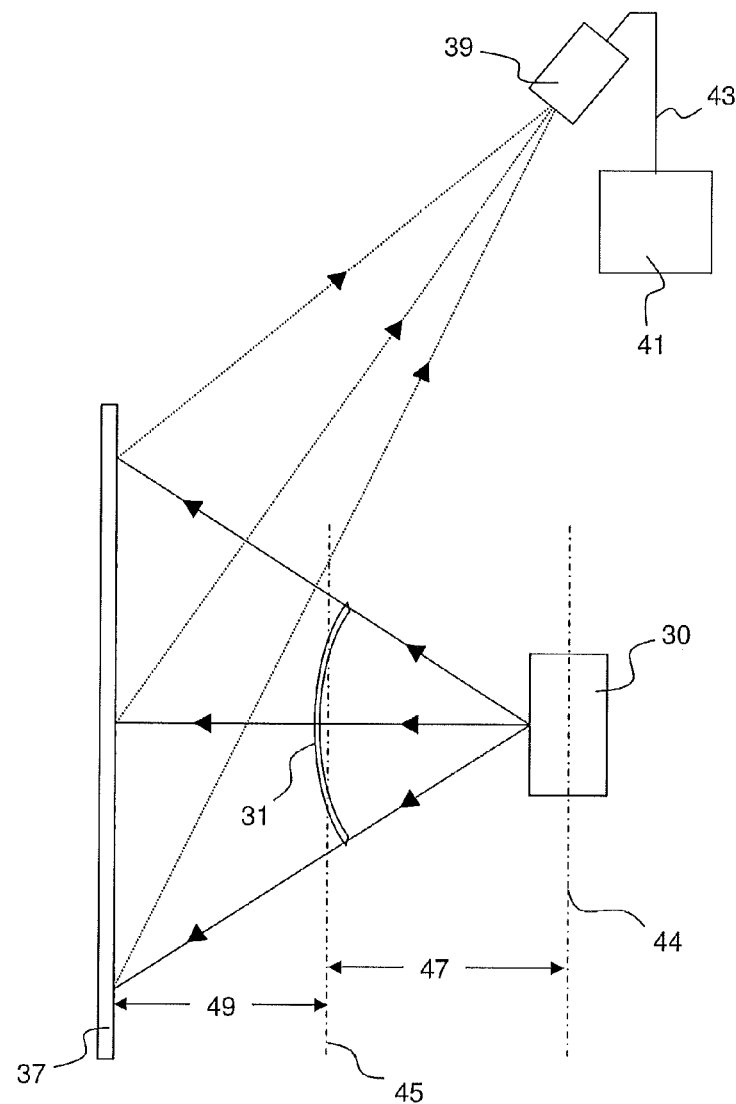

FIG. 3b shows a plan view of the apparatus shown in FIG. 3a. The line 44 represents an axis that is coincident with the lamp 30, and is parallel to the screen 37. The line 45 represents an axis that runs through the heatable vehicle glazing and is parallel to the heatable vehicle windscreen 37 and the line 44. The separation of the lamp 30 and the heatable vehicle windscreen 31 is represented by the distance 47 and is in the region of 3 m to 4 m when measurements are made. The distance of the heatable vehicle windscreen 31 from the screen 37 when measurements are made is represented by the distance 49 and is in the region of 1 m to 2 m.

FIG. 4 shows a shadowgraph image of a heatable vehicle windscreen when no electrical current is passing through the heater wires of the heater array. The image shows a portion of the black obscuration band 51 and a portion 53 of the central region of the windscreen. The individual wires in the array of heater wires are not able to be sufficiently resolved such that the shadowgraph image is not usable for subsequent calculations. Such a shadowgraph image may however be used as a reference shadowgraph image for use in subsequent calculations.

FIG. 5 shows a shadowgraph image of the same heatable vehicle windscreen used to produce the reference shadowgraph image of FIG. 4, except the heater array is connected to an electrical power supply. There is sufficient electrical current passing through the heater wires in the heater array such that the heater wires are easily observable in the shadowgraph image. Such a shadowgraph image is referred to as an active shadowgraph image. The active shadowgraph image shows the black obscuration band 51, a portion 55 of the heatable windscreen wherein there are no heater wires and a region 57 of the heatable windscreen wherein there is a portion of the heater array of heater wires. Within the region 57 there are a number of substantially parallel heater wires 59. The heater wires have an approximate sinusoidal configuration, but the heater wires may be linear. The active shadowgraph image clearly shows a region 60 bounded by two heater wires wherein no heater wire is visible in the active shadowgraph image. This may be due to there being no heater wire present in the heater array in that region, or there may be an electrical connection problem preventing electrical current from passing through the wire in that region. In any event, such a region void of a heater wire may be unacceptable to the function of the heater array because the heater array may not produce the required heating effect to adequately de-ice or demist the windscreen in that region.

In an alternative embodiment, the active shadowgraph image of the heatable glazing may be formed without the use of a screen. Such a technique is known as "Focused" Shadowgraphy and is described in the text book "Schlieren and Shadowgraph Techniques—Visualizing Phenomena in Transparent Media; pp. 155-159; G. S. Settles; Springer-Verlag; (2001); ISBN 3-540-66155-7". The technique as applied to the present invention is described with reference to FIG. 6.

Figure 6:
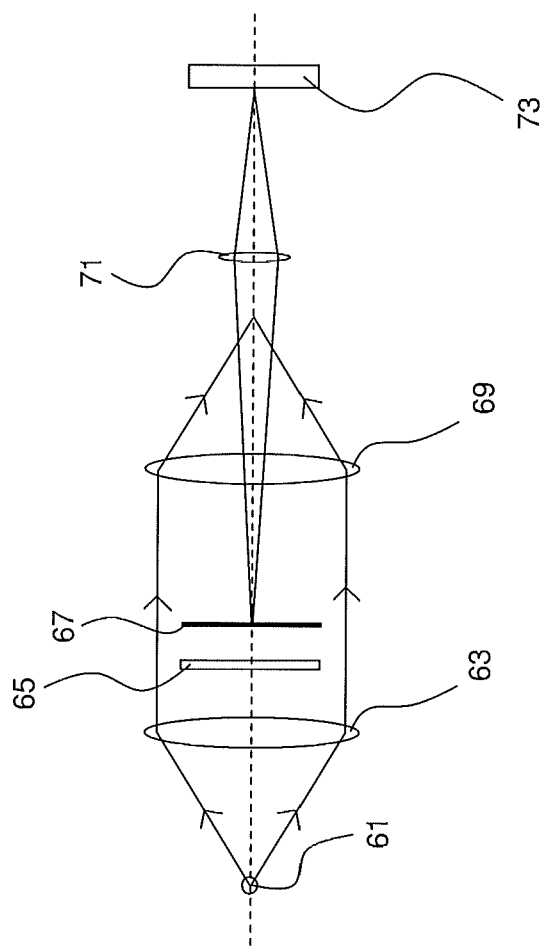
FIG. 6 shows an arrangement for measuring a shadowgraph image of a heatable vehicle windscreen without the use of a screen but instead focussing on a plane in space.

In FIG. 6, light from a light source 61 is directed onto lens 63 to produce a collimated beam of light. A suitable light source is a light emitting diode (LED). The collimated beam of light is directed towards the heatable glazing 65 (of the type described with reference to FIG. 1) and a shadowgraph image of the glazing is produced at plane 67. The light is then collected by lens 69. A focussing lens 71 is used to image the shadowgraph at the plane 67 onto an imaging sensor 73 such as a camera, in particular a digital camera. An advantage of this technique is that dark room conditions are not required. The lenses 63, 69 may be replaced by suitable mirrors.

The shadowgraph image at plane 67 may be acquired in a single exposure or in a strip-like fashion by using a suitable lens/mirror/light arrangement. For example, by using strip mirrors a strip of collimated light may be produced and the glazing 65 may be moved relative to the strip of collimated light such that only a portion of the glazing is illuminated at a time. A suitable strip-like detector may be used to image the portion of the shadowgraph thereby produced at plane 67. The entire shadowgraph image may be formed by collecting the appropriate number of portions.

The active shadowgraph image obtained by the focussed shadowography technique (i.e. without projection onto a screen) may be analysed in the same way as the shadowgraph image obtained by projecting the shadowgraph onto a screen.

Again, a reference shadowgraph image of the glazing may be obtained using the apparatus shown in FIG. 6 by making measurements without the heater array being connected to a power supply such that the heater wires are at ambient temperature.

In one embodiment of the first aspect of the present invention, the active shadowgraph image obtained when sufficient electrical current is passed through the heater array such that the heater wires are observable in the shadowgraph image may be used for subsequent calculations. When projected onto a screen, the active shadowgraph image may be inspected manually and the number of non-functioning heater wires determined. Preferably the active shadowgraph image is captured by a camera and subsequently analysed. The analysis may be carried out manually, but it is preferred that the subsequent analysis be carried out by a computer.

Figure 7:
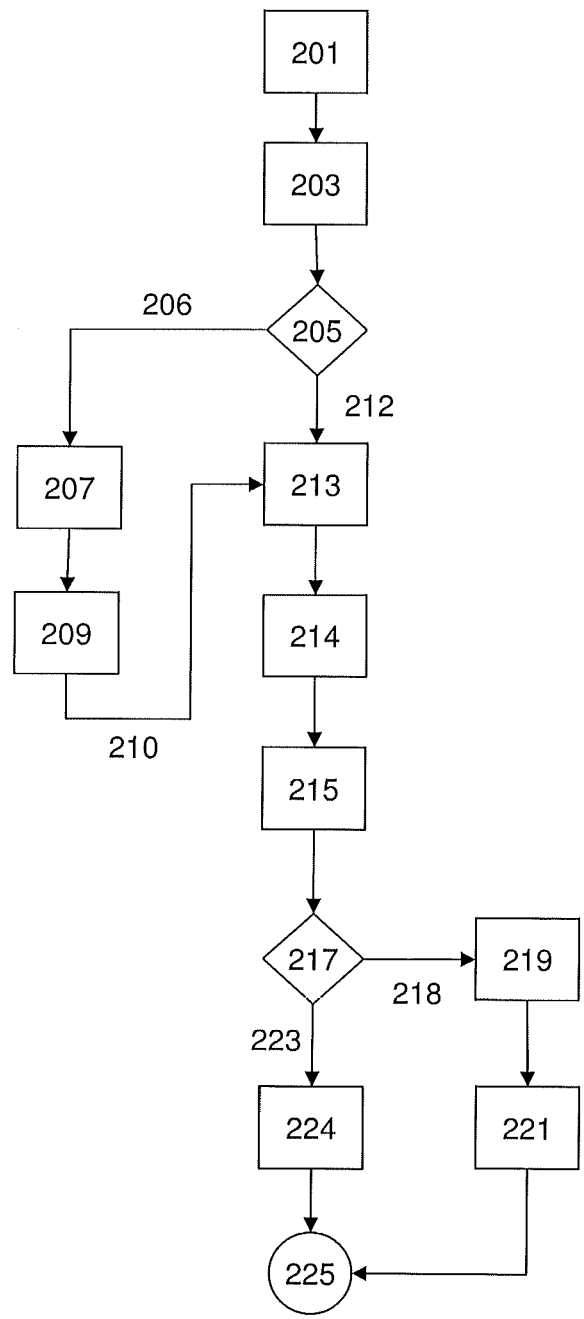
FIG. 7 illustrates the steps involved in determining the characteristics of a heater array that is part of a heatable glazing.

A method in accordance with the first aspect of the invention shall now be described with reference to FIG. 7. FIG. 7 is a block diagram illustrating the steps involved in a method of inspecting a heatable glazing according the first aspect of the invention.

At step 201, a heatable glazing comprising a heater array having at least one heater wire is positioned such that the glazing may be illuminated by a suitably positioned light source. At this step, an imaging sensor is also suitably located such that light transmitted through the glazing, thereby producing a shadowgraph image of the glazing, may be collected by the imaging sensor, either by direct illumination thereof or by capturing the reflection of the shadowgraph image off a screen. Preferably the imaging sensor is a digital camera.

The method then moves to step 203. With no power supply connected to the heater array such that no electrical current passes through the heater wires, the heatable glazing is illuminated with the light source thereby producing a shadowgraph image of the heatable glazing.

Step 205 is a decision point wherein it is decided whether a reference shadowgraph image of the glazing should be measured in addition to an active shadowgraph image of the heatable glazing. If a reference shadowgraph image of the glazing is to be measured, path 206 is followed.

At step 207, the shadowgraph image is captured by the imaging sensor.

At step 209, the shadowgraph image captured in step 207 is stored in a computer and set as the reference shadowgraph image of the heatable glazing. The method then follows path 210 to step 213.

If no reference shadowgraph is to be measured, decision point 205 follows path 212 to step 213.

Since the heatable glazing is already illuminated at step 203, the illumination conditions when the active shadowgraph image is captured will be the same, or substantially the same, as the illumination conditions when the reference shadowgraph image was captured. When a reference shadowgraph image and an active shadowgraph image are measured, by having the same, or substantially the same, illumination conditions, it is much simpler to compensate the active shadowgraph image for the reference shadowgraph image.

At step 213, the heater array of the heatable glazing is connected to a suitable power supply and an electrical current is passed through the heater array. Sufficient electrical current should be passed through the heater array such that the heater wires are observable in the shadowgraph image produced when the heatable glazing is illuminated by the light source. Too high an electrical current may damage the heater wires.

At step 214, with the heater wires observable in the shadowgraph image, the shadowgraph image of the heatable glazing is captured by the imaging sensor.

At step 215, the shadowgraph image captured in step 214 is stored in a computer and set as the active shadowgraph image of the heatable glazing.

Step 217 is another decision point wherein subsequent analysis of the shadowgraph image or images captured in the preceding steps depends on whether a reference shadowgraph image was measured or not. If a reference shadowgraph image was measured, path 218 is followed.

At step 219, the optical effects in the active shadowgraph image produced by other artefacts not related to the heater array, for example dust on one of the surfaces of the heatable glazing are reduced or effectively eliminated by correction of the active shadowgraph image with respect to the reference shadowgraph image. This may be done by dividing the active shadowgraph image by the reference shadowgraph image or subtracting the reference shadowgraph image from the active shadowgraph image. This operation is carried out at step 219 to produce what shall be referred to as a difference shadowgraph image of the heatable glazing.

At step 221, the difference shadowgraph image of the heatable glazing is analysed.

If no reference shadowgraph image was measured, decision point 217 follows path 223.

At step 224, the active shadowgraph image is analysed. The analysis routine used to analyse the active shadowgraph image at step 224 may be the same as the analysis routines used to analyse the difference shadowgraph image at step 221.

At step 225, the results of the analysis are presented such that the relevant parameters of the heater array of the heatable glazing may be compared with the specification for such parameters.

The exact analysis carried out on the difference shadowgraph image at step 221 or the active shadowgraph image at step 224 depends upon the characteristics of the heater array that are important. Different characteristics may have a different degree of importance depending upon the particular application of the heatable glazing.

At step 221 or 224 the shadowgraph image may be thresholded using conventional thresholding techniques. The thresholded image may then be subsequently analysed.

Figure 8:
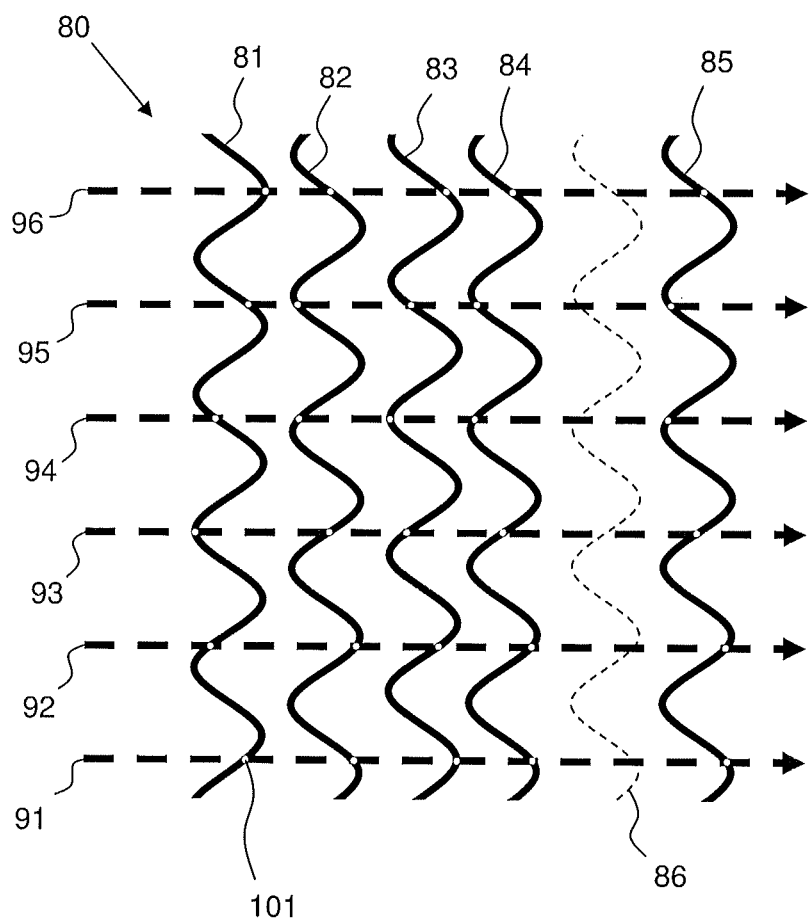
FIG. 8 illustrates one method for analysing the shadowgraph image of the heatable vehicle windscreen.

One possible technique is to analyse the thresholded shadowgraph image using a number of parallel linescans across the image, as illustrated in FIG. 8.

FIG. 8 shows a portion of an active shadowgraph or difference shadowgraph image that has been thresholded such that the wires arc distinguishable from the background. There are five heater wires shown, 81, 82, 83, 84 and 85. A heater wire was not observable in the active shadowgraph image of the heater array and is shown as a dotted line 86; this heater wire was missing from the shadowgraph image of the array, for example as described with reference to region 60 of FIG. 4. There are six linescans shown as dashed lines 91, 92, 93, 94, 95 and 96. Each linescan consists of a number of pixels.

Using a linescan approach, the intersection of each heater wire with each linescan can be found. For example, with reference to FIG. 8, the linescan 91 intersects the wire 81 at the point 101 as indicated by the white dot. The intersection of the linescans with the heating wires is indicated by a white dot at the point of intersection. For the portion of the heater array shown in FIG. 8, the spacing of the heater wires is non-uniform and there is a missing wire (as indicated by the dotted line 86). The uniformity of the heater wire spacing may be within a predetermined specification for the spacing of the heater wires in the heater array.

Depending upon the configuration of the obscuration band, as illustrated by FIG. 2, part of the heater array at the upper centre may be obscured by a region of black print. Such a region is used when additional components are bonded to the inner surface of the glazing, for example a rear view mirror stem. When the obscuration band extends into the heater array as shown in FIG. 2, it is not possible to directly measure the shadowgraph image of the heater wires in this region. One option is to simply ignore measurements of the regions adjacent to the printed region. Another option is to consider regions either side of the printed region and measure those regions alone. For a particular glazing, acceptable characteristics of the heater array in these regions could be defined.

Another alternative is to extrapolate the heater wires into the region wherein measurement is not possible. To extrapolate reliably, it may be necessary to increase the number of linescan measurements.

Although in the previous figures the heater wires are shown as having an undulating form, the heater wires may be linear.

Methods in accordance with the first aspect of the invention may be useful in detecting non-working electrical conductors that are incorporated into a laminated construction. For example, the technique may be useful with certain laminated antennae systems.

Additionally, any electrical conductor that is embedded in an optically transparent glazing medium could be assessed by measuring a shadowgraph image of the glazing when sufficient electrical current passes through the electrical conductor such that the electrical conductor is observable in the shadowgraph image. For example, the glazing may have an outer surface of a plastics material such as polycarbonate. Alternatively, the glazing may be a bilayer construction, for example consisting of a sheet of glass with a layer of PVB. The electrical conductor may be embedded in the body of the glazing medium, for example a panel made of a suitable plastic material.

The invention claimed is:

1. A method of inspecting a heatable glazing, the heatable glazing comprising two plies and a heater array including a heater wire disposed between the two plies, the method comprising the steps
   (i) illuminating the heatable glazing with a light source to produce a shadowgraph image of the heatable glazing;
   (ii) passing a sufficiently high electrical current through the heater array such that the heater wire gets hot and the refractive index of medium of the glazing surrounding the heater wire changes allowing the heater wire to be observable in the shadowgraph image of the heatable glazing, such a shadowgraph image of the heatable glazing being referred to as an active shadowgraph image of the heatable glazing; and
   (iii) capturing the active shadowgraph image of the heatable glazing with an imaging sensor.

2. A method according to claim 1, wherein the active shadowgraph image is projected onto a screen and the imaging sensor captures the active shadowgraph image that is projected onto the screen.

3. A method according to claim 1, wherein the active shadowgraph image is projected onto a plane in space, and the imaging sensor focuses onto the plane in space to capture the active shadowgraph image.

4. A method according to claim 1, comprising the step of illuminating the glazing when insufficient electrical current is passing through the heater array such that the heater wire is not observable in the shadowgraph image, thereby producing a reference shadowgraph image of the heatable glazing, capturing the reference shadowgraph image, and comparing the active shadowgraph image of the heatable glazing with the reference shadowgraph image of the heatable glazing.

5. A method according to claim 4, wherein the step of comparing the active shadowgraph image of the heatable glazing with the reference shadowgraph image of the heatable glazing comprises subtracting the reference shadowgraph image of the heatable glazing from the active shadowgraph image of the heatable glazing.

6. A method according to claim 4, wherein the step of comparing the active shadowgraph image of the heatable glazing with the reference shadowgraph image of the heatable glazing comprises dividing the active shadowgraph image of the heatable glazing by the reference shadowgraph image of the heatable glazing.

7. A method according to claim 4, wherein no electrical current passes through the heater array when the reference shadowgraph image is produced.

8. A method according to claim 4, wherein the reference shadowgraph image is captured before the active shadowgraph image.

9. A method according to claim 1, wherein the heater array comprises a plurality of heater wires.

10. A method according to claim 9, wherein the average spacing of the heater wires is determined.

11. A method according to claim 1, wherein the existence of a nonfunctioning heater wire is determined.

12. A method according to claim 1, wherein the imaging sensor is part of a camera, preferably a digital camera.

13. An apparatus for inspecting a heater wire laminated within a heatable glazing, the apparatus comprising a light source for illuminating the heatable glazing to produce a shadowgraph image of the glazing, an imaging sensor to acquire the shadowgraph image and a power supply for applying sufficient electrical current to the heater wire such that the heater wire gets hot and the refractive index of medium of the glazing surrounding the heater wire changes allowing the heater wire to be observable in the shadowgraph image of the glazing.

14. The method of claim 1, wherein the two plies are glass plies.

* * * * *